United States Patent [19]
Kunimi et al.

[11] Patent Number: 5,831,041
[45] Date of Patent: Nov. 3, 1998

[54] MONOAZO COMPOUNDS AND DYEING OR PRINTING PROCESS FOR FIBER MATERIALS USING THEM

[75] Inventors: Nobutaka Kunimi, Toyonaka; Toshiyuki Araki; Yasuyoshi Ueda, both of Hirakata, all of Japan

[73] Assignee: Sumitomo Chemical Company, Limited, Osaka, Japan

[21] Appl. No.: 954,518

[22] Filed: Oct. 20, 1997

Related U.S. Application Data

[63] Continuation of Ser. No. 749,113, Nov. 14, 1996, abandoned.

[30] Foreign Application Priority Data

Nov. 14, 1995 [JP] Japan ................................. 7-295432

[51] Int. Cl.$^6$ .............................. C09B 62/51; D06P 1/384
[52] U.S. Cl. ............................................ 534/641; 534/640
[58] Field of Search ....................................... 534/640, 641

[56] References Cited

U.S. PATENT DOCUMENTS

| | | | |
|---|---|---|---|
| 4,754,023 | 6/1988 | Tzikas et al. | 534/641 X |
| 5,138,041 | 8/1992 | Buch et al. | 534/642 |
| 5,597,902 | 1/1997 | Bootz et al. | 534/638 X |

FOREIGN PATENT DOCUMENTS

| | | |
|---|---|---|
| 58-065759 | 4/1983 | Japan . |
| 58-071957 | 4/1983 | Japan . |

*Primary Examiner*—Fiona T. Powers
*Attorney, Agent, or Firm*—Stevens, Davis, Miller & Mosher, L.L.P.

[57] ABSTRACT

A monoazo compound represented by the general formula (I):

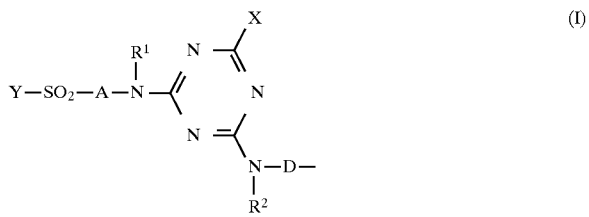

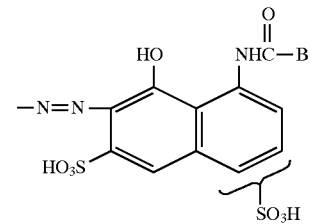

wherein A represents alkylene which may be substituted or a group: —$(CH_2)_m$—$Q^1$—$(CH_2)_n$— wherein $Q^1$ is —O—, —S— or —$NR^3$—, m and n are, independently with each other, 2, 3 or 4 and $R^3$ is hydrogen, alkyl which may be substituted or phenyl which may be substituted; B represents β-carboxyvinyl, alkyl which may be substituted or phenyl which may be substituted; D represents phenylene which may be substituted; X represents aliphatic, aromatic, alicyclic, cyclic or unsubstituted amino; $R^1$ and $R^2$ represent, independently with each other, hydrogen or alkyl which may be substituted; and $SO_2Y$ is a reactive vinyl sulfone group; or a salt thereof, and a process for dyeing or printing fiber materials using said compound. Said process enables red dyeing or printing of hydroxyl group and/or amido group containing organic materials with excellent fixing in deep dyeing.

10 Claims, No Drawings

MONOAZO COMPOUNDS AND DYEING OR PRINTING PROCESS FOR FIBER MATERIALS USING THEM

This application is a continuing application of Ser. No. 08/749,113, filed Nov. 14, 1996, now abandoned.

BACKGROUND OF THE INVENTION

1. Field of the Invention

The present invention relates to fiber-reactive monoazo compounds which are suitable for use as fiber-reactive red dyes in dyeing and printing organic materials containing a hydroxyl group and/or amido group, particularly materials such as cellulose fibers, natural and synthetic polyamide fibers, polyurethane fibers, leathers or the like, and mixed yarn thereof.

2. Background Information

Monoazo compounds having an aliphatic vinyl sulfone reactive group are disclosed in JP-A-58-65759, JP-B-60-17457 and others.

While various reactive dyes have been generally used in the field of dyeing and printing, the level of current technique is not satisfactory in view of higher level of demand on dyeing performance and elevating level of demand on dyeing fastness. Among others, excellent build-up properties have become very important in recent days when the level of demand on dyeing economy is more and more elevating. That is, high build-up properties of dyes has become an important subject in a deep color dyeing in order to reduce coloring of waste water from dyeing.

As the result of an extensive study for finding out novel red-dyeing fiber-reactive compounds having excellent build-up properties, the present inventors have found that a certain kind of monoazo compounds is excellent in the properties. The present invention has been completed on the basis of such finding.

SUMMARY OF THE INVENTION

The present invention provides a monoazo compound represented by the general formula (I):

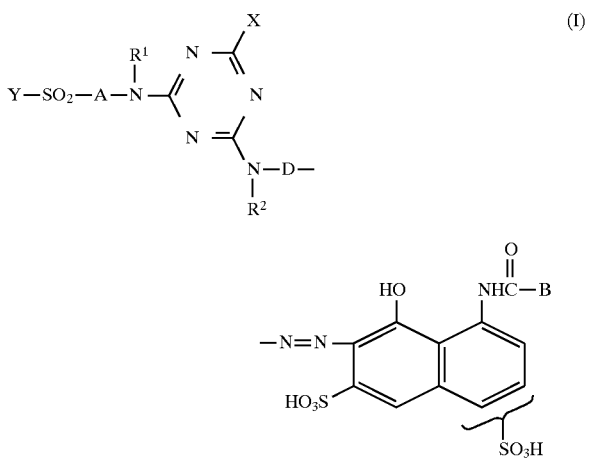

wherein A represents alkylene which may be substituted or a group: —(CH$_2$)m—Q$^1$—(CH$_2$)n—
wherein Q$^1$ is —O—, —S— or —NR$^3$—, m and n are, independently with each other, 2, 3 or 4 and R$^3$ is hydrogen, alkyl which may be substituted or phenyl which may be substituted; B represents β-carboxyvinyl, alkyl which maybe substituted or phenyl which may be substituted; D represents a group of the formula (II):

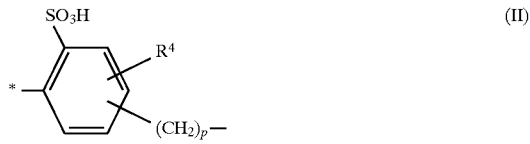

wherein * represents a bond connecting to the azo group in the formula (I), R$^4$ is hydrogen, methyl or methoxy and p is 0 or 1;

X represents a group of the formula (III) or (IV):

wherein R$^5$ and R$^6$ are, independently with each other, hydrogen, alkyl which may be substituted, phenyl which may be substituted or naphthyl which may be substituted, r is 1, 2 or 3, Q$^2$ is —O—, —S—, —CH$_2$—, —SO$_2$— or —NR$^7$— in which R$^7$ is hydrogen or alkyl which may be substituted; R$^1$ and R$^2$ are, independently with each other, hydrogen or alkyl which may be substituted; and Y is a group: —CH=CH$_2$ or —CH$_2$CH$_2$Z wherein Z is a sulfate ester, a thiosulfate ester, a phosphate ester, an acetate ester or a halogen atom; or a salt thereof.

In this specification, including the accompanying claims, the alkyl groups or moieties may be straight or branched chain.

The present invention also provides a process for dyeing or printing a fiber material using a monoazo compound of the above formula (I) or a salt thereof.

DETAILED DESCRIPTION OF THE INVENTION

In the general formula (I), alkylene which may be substituted and is represented by A, includes C$_2$-C$_4$ alkylene which may be substituted with a substituent selected from the group consisting of C$_1$-C$_4$ alkyl, halogeno, hydroxy, sulfo, cyano, C$_3$-C$_4$ alkoxy, C$_1$-C$_4$ alkoxycarbonyl, C$_1$-C$_4$ alkylcarbonyloxy and carbamoyl. Among them, unsubstituted C$_2$-C$_4$ alkylene, particularly ethylene and trimethylene, are preferred.

When A is a group: —(CH$_2$)m—Q$^1$—(CH$_2$)n— wherein Q$^1$ is —NR$^3$—, preferred R$^3$ includes hydrogen, C$_1$-C$_4$ alkyl, phenyl which may be substituted with sulfo, and the like, among which hydrogen, methyl and ethyl are preferred.

Among the group: —(CH$_2$)m—Q$^1$—(CH$_2$)n— represented by A, particularly preferred examples include those wherein Q$^1$ is —O— and m and n are, independently with each other, 2 or 3. Specifically the preferred examples include the following groups:

—CH$_2$CH$_2$—O—CH$_2$CH$_2$—,
—CH$_2$CH$_2$—O—CH$_2$CH$_2$CH$_2$— and
—CH$_2$CH$_2$CH$_2$—O—CH$_2$CH$_2$CH$_2$— wherein any one of the free ends in the formula may be attached to the group SO$_2$ in the formula (I).

Among the groups represented by A, particularly preferred are ethylene, trimethylene and —CH$_2$CH$_2$—O—CH$_2$CH$_2$—.

Alkyl which may be substituted and is represented by B includes C$_1$–C$_4$ alkyl which may be substituted with a substituent selected from the group consisting of C$_1$–C$_4$ alkyl, C$_1$–C$_4$ alkoxy, carboxy, halogeno, hydroxy, sulfo, cyano, C$_1$–C$_4$ alkoxycarbonyl, C$_1$–C$_4$ alkylcarbonyloxy and carbamoyl. Among them, preferred examples include methyl, ethyl, n— or iso-propyl, 2-carboxyethyl, chloromethyl and 2-chloroethyl.

Phenyl which may be substituted and is represented by B includes phenyl which may be substituted with one or two substituents selected from the group consisting of C$_1$–C$_4$ alkyl, C$_1$–C$_4$ alkoxy, carboxy, halogeno, hydroxy, sulfo, cyano, nitro, amino, C$_1$–C$_4$ alkoxycarbonyl, C$_1$–C$_4$ alkylcarbonyloxy, carbamoyl and sulfamoyl. Among them, preferred examples include phenyl, 2-chlorophenyl, 3-chlorophenyl, 4-chlorophenyl, 2-nitrophenyl, 3-nitrophenyl, 4-nitrophenyl, 2-sulfophenyl, 3-sulfophenyl, 4-sulfophenyl, 2-carboxyphenyl, 3-carboxyphenyl, 4-carboxyphenyl, 2,4-dichlorophenyl, 2,5-dichlorophenyl, 3,5-dichlorophenyl and the like.

Examples of groups of the formula (II) represented by D include the following groups:

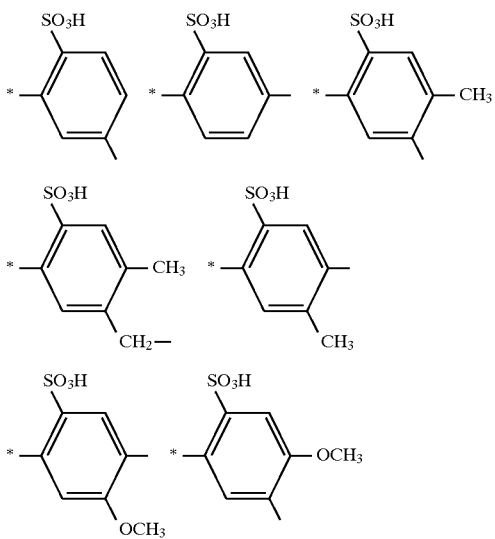

wherein * is as described above.

Among them, preferred D includes 2-sulfo-1,5-phenylene which is connected to the azo group through the position 1 or the like.

When X is the group —NR$^5$R$^6$ of the above described formula (III), and R$^5$ and/or R$^6$ is alkyl which may be substituted, preferred examples of the alkyl include C$_1$–C$_5$ alkyl, such as C$_1$–C$_4$ alkyl, which may be substituted with one or two substituents selected from the group consisting of C$_1$–C$_4$ alkoxy, sulfo, carboxy, sulfamoyl, carbamoyl, hydroxy, halogeno, cyano, vinyl, carboxylate ester, sulfate ester, acetylamino, dimethylamino, phenyl which may be substituted and sulfato. When R$^5$ and/or R$^6$ is alkyl substituted with phenyl (e.x. benzyl) which may be substituted, such alkyl is preferably methyl and such phenyl may be substituted with one or two substituents selected from the group consisting of C$_1$–C$_4$ alkyl, C$_1$–C$_4$ alkoxy, sulfo and halogeno.

When X is the group —NR$^5$R$^6$ of the above described formula (III) and R$^5$ and/or R$^6$ is alkyl which may be substituted, particularly preferred examples of the alkyl include methyl, ethyl, n-propyl, isopropyl, n-butyl, isobutyl, sec-butyl, βhydroxyethyl, β-sulfatoethyl, β-sulfoethyl, β-methoxyethyl, β-carboxyethyl, β-carbamoylethyl, βsulfamoylethyl, benzyl, 2-sulfobenzyl, -3-sulfobenzyl and 4-sulfobenzyl.

When X is the group —NR$^5$R$^6$ of the above described formula (III)and R$^5$ and/or R$^6$ is phenyl which may be substituted, preferred examples of the phenyl include phenyl which may be substituted with one or two substituents selected from the group consisting of C$_1$–C$_4$ alkyl, C$_1$–C$_4$ alkoxy, sulfo, carboxy, halogeno (chloro, bromo, fluoro and the like), hydroxy, cyano, carbamoyl, sulfamoyl, carboxylate ester, methane sulfonyl, β-hydroxyethylsulfonyl, amino, acylamino and alkyl- (particularly C$_1$–C$_4$ alkyl) substituted amino. Among them, particularly preferred examples include phenyl, 2- methylphenyl, 3-methylphenyl, 4-methylphenyl, 2-methoxyphenyl, 3-methoxyphenyl, 4-methoxyphenyl, 2-ethylphenyl, 3-ethylphenyl, 4-ethylphenyl, 2-ethoxyphenyl, 3-ethoxyphenyl, 4-ethoxyphenyl, 2-carboxyphenyl, 3-carboxyphenyl, 4-carboxyphenyl, 2-chlorophenyl, 3-chlorophenyl, 4-chlorophenyl, 2-sulfophenyl, 3-sulfophenyl, 4-sulfophenyl, 3-sulfo-4-methoxyphenyl, 2-hydroxyphenyl, 3-hydroxyphenyl and 4-hydroxyphenyl.

When X is the group —NR$^5$R$^6$ of the above described formula (III) and R$^5$ and/or R$^6$ is naphthyl which may be substituted, preferred examples of the naphthyl include naphthyl which may be substituted with one, two or three substituents selected from the group consisting of C$_1$–C$_4$ alkyl, C$_1$–C$_4$ alkoxy, sulfo, carboxy, halogeno (chloro, bromo and the like) and hydroxy. Among them, particularly preferred examples include 2-sulfo-1-naphthyl, 3-sulfo-1-naphthyl, 4-sulfo-1-naphthyl, 5-sulfo-1-naphthyl, 6-sulfo-1-naphthyl, 7-sulfo-1-naphthyl, 8-sulfo-1-naphthyl, 1-sulfo-2-naphthyl, 5-sulfo-2-naphthyl, 6-sulfo-2-naphthyl, 7-sulfo-2-naphthyl, 8-sulfo-2-naphthyl, 1,5-disulfo-2-naphthyl, 5,7-disulfo-2-naphthyl, 6,8-disulfo-2-naphthyl, 4,8-disulfo-2-naphthyl, 4,7-disulfo-2-naphthyl, 3,8-disulfo-2-naphthyl, 4,6-disulfo-2-naphthyl, 3,7-disulfo-2-naphthyl, 3,6-disulfo-2-naphthyl, 4,6,8-trisulfo-1-naphthyl, 2,4,7-trisulfo-1-naphthyl, 3,6,8-trisulfo-1-naphthyl, 1,5,7-trisulfo-2-naphthyl, 4,6,8-trisulfo-2-naphthyl, 3,6,8-trisulfo-2-naphthyl and the like.

When X is a group of the above described formula (IV) wherein Q$^2$ is —NR$^7$—, preferred examples for R$^7$ include hydrogen and C$_1$–C$_4$ alkyl, and particularly hydrogen, methyl and ethyl are preferred.

When X is a group of the above described formula (IV), examples include residues derived from pyrrolidine, piperidine, piperazine, N-alkylpiperazine, morpholine and the like. Among them, particularly preferred are groups of formula (IV) in which r is 2 and Q$^2$ is —O— or —CH$_2$—, i.e. morpholino and piperidino.

Among those mentioned above, preferred X is a group of the above described formula (III) and particularly that wherein one of R$^5$ and R$^6$ is phenyl which may be substituted. More particularly preferred are groups wherein R$^5$ is hydrogen, methyl or ethyl and R$_6$ is phenyl which may be substituted with C$_1$–C$_4$ alkyl, C$_1$–C$_4$ alkoxy, sulfo, carboxy, halogeno, hydroxy, cyano or acylamino.

When X is the group —NR$^5$R$^6$ of the above described formula (III), examples of amine of the formula: HNR$^5$R$^6$ include ammonia;

aromatic amines such as 1-aminobenzene, 1-amino-2-, -3-, or -4-methylbenzene, 1-amino-2,4-, -3,4-, or -3,5-dimethylbenzene, 1-amino-2-, -3-, or -4-methylbenzene, 1-amino-2-, -3-, or -4-methoxybenzene, 1-amino-2-, -3-, or -4-ethoxybenzene, 1-amino-2-, -3-, or -4-chlorobenzene, 1-amino-2-, -3-, or -4-bromobenzene, 1-amino-2-, -3-, or -4-fluorobenzene, 3-or 4-aminophenyl-methanesulfonic acid, 2-, 3- or 4-aminobenzenesulfonic acid, 3- or 4-methylaminobenzene-sulfonic acid, 3- or 4-ethylamino-benzenesulfonic acid, 5-aminobenzene-1,3-disulfonic acid, 6-aminobenzene-1,3- or -1,4-disulfonic acid, 4-aminobenzene-1,2-disulfonic acid, 4-amino-5-methylbenzene-1,2-disulfonic acid, 2-, 3-or 4-aminobenzoic acid, 5-aminobenzene-1,3-dicarboxylic acid, 5-amino-2-hydroxy-benzenesulfonic acid, 4-amino-2-hydroxy-benzenesulfonic acid, 5-amino-2-ethoxy-benzenesulfonic acid, N-methylaminobenzene, N-ethylaminobenzene, 1-methylamino-3- or -4-methylbenzene, 1-ethylamino-3- or -4-methylbenzene, 1-methylamino-2-, -3-or-4-chlorobenzene, 1-ethylamino-2-, -3- or --4-chlorobenzene, 1-(2-hydroxyethyl)amino-3-methylbenzene, 3- or 4-methylaminobenzoic acid, 1-amino-2-methoxy-5-methylbenzene, 1-amino-2,5-dimethoxybenzene, 2-, 3- or 4-aminophenol, 1-amino-3- or 4-acetylaminobenzene, 2,4- or 2,5-diaminobenzenesulfonic acid, 1-aminobenzene-3- or -4-(β-hydroxyethylsulfone), 2-, 4-, 5-, 6-, 7- or 8-aminonaphthalene-1-sulfonic acid, 1-, 4-, 5-, 6-, 7- or 8-aminonaphthalene-2-sulfonic acid, 7-methylaminonaphthalene-2-sulfonic acid, 7-ethylaminonaphthalene-2-sulfonic acid, 7-propylaminonaphthalene-2-sulfonic acid, 7-butylamino-naphthalene-2-sulfonic acid, 7-isobutylaminonaphthalene-2-sulfonic acid, 4-, 5-, 6-, 7- or 8-aminonaphthalene-1,3-disulfonic acid, 2-, 3- or 4-aminonaphthalene-1,5-disulfonic acid, 4- or 8-aminonaphthalene-1,6-disulfonic acid, 4-aminonaphthalene-1,7-disulfonic acid, 3- or 4-aminonaphthalene-2,6-disulfonic acid, 3- or 4-aminonaphthalene-2,7-disulfonic acid, 6- or 7-aminonaphthalene-1,3,5-trisulfonic acid, 4-, 7- or 8-aminonaphthalene-1,3,6-trisulfonic acid and 4-aminonaphthalene-1,3,7-trisulfonic acid; and aliphatic amines such as methylamine, ethylamine, n-propylamine, isopropylamine, n-butylamine, isobuylamine, sec-butylamine, dimethylamine, diethylamine, methylethylamine, allylamine, 2-chloroethylamine, 2-methoxyethylamine, 2-aminoethanol, 2-methylaminoethanol, bis(2-hydroxyethyl)amine, 2-acetylaminoethylamine, 1-amino-2-propanol, 3-methoxypropylamine, 1-amino-3-dimethylaminopropane, 2-aminoethanesulfonamide, 2-aminoethanesulfonic acid, aminomethanesulfonic acid, 2-methylaminoethanesulfonamide, 2-methylaminoethanesulfonic acid, 3-amino-1-propanesulfonic acid, 2-sulfatoethylamine, aminoacetic acid, methylaminoacetic acid, 3-aminopropionic acid, 3-aminopropinamide, 3-methylaminopropionic acid, 3-methylamino-propionamide, ε-aminocaproic acid, benzylamine, 2-, 3- or 4-sulfobenzylamine, 2-, 3- or 4-chlorobenzylamine, 2-, 3- or 4-methylbenzylamine, N-methylbenzylamine, 1-phenylethylamine, 2-phenylethylamine and 1-phenyl-2-propylamine.

Among them, particularly preferred compounds of the formula: $HNR^5R^6$ include, for example, aniline, N-methylaniline, N-ethylaniline, 2-, 3- or 4-chloroaniline, N-methyl-2-, -3- or -4-chloroaniline, N-ethyl-2-, -3- or -4-chloroaniline, 2-, 3- or 4-methylaniline, 2-, 3- or 4-ethylaniline 2-, 3- or 4-methoxyaniline-, 2-, 3- or 4-ethoxyaniline, 2-, 3- or 4-hydroxyaniline, aniline-2-, -3- or -4-sulfonic acid, 3-- or 4-methylaminobenzenesulfonic acid, 3- or 4-ethylaminobenzene-sulfonic acid, 2-, 3- or 4-carboxyaniline, ammonia, methylamine, ethylamine, dimethylamine, taurine, N-methyltaurine, mono- or di-ethanolamine; 2-sulfamoylethylamine and 2-carbamoylethylamine. Particularly preferred are aniline and derivatives thereof.

Alkyl which may be substituted and is represented by $R^1$ and $R^2$ is preferably $C_1$–$C_4$ alkyl which may be substituted. The preferred substituents include, for example, hydroxy, cyano, $C_1$–$C_4$ alkoxy, halogeno, carbamoyl, carboxy, alkoxycarbonyl, alkylcarbonyloxy, sulfo and sulfamoyl. More specific, preferred $R^1$ and $R^2$ include, for example, hydrogen, methyl, ethyl, n-propyl, isopropyl, n-butyl, isobutyl, sec-butyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 3,4-dihydroxybutyl, cyanomethyl, 2-cyanoethyl, 3-cyanopropyl, methoxymethyl, ethoxymethyl, 2-methoxyethyl, 2-ethoxyethyl, 3-methoxypropyl, 3-ethoxypropyl, 2-hydroxy-3-methoxypropyl, chloromethyl, bromomethyl, 2-chloroethyl, 2-bromoethyl, 3-chloropropyl, 3-bromopropyl, 4-chlorobutyl, 4-bromobutyl, carboxymethyl, 2-carboxyethyl, 3-carboxypropyl, 4-carboxybutyl, 1,2-dicarboxy-ethyl, carbamoylmethyl, 2-carbamoylethyl, 3-carbamoylpropyl, 4-carbamoylbutyl, methoxycarbonylethyl, ethoxycarbonylmethyl, 2-methoxycarbonylmethyl, 2-ethoxycarbonylethyl, 3-methoxycarbonylpropyl, 3-ethoxycarbonylpropyl, 4-methoxycarbonylbutyl, 4-ethoxycarbonylbutyl, methylcarbonyloxymethyl, ethylcarbonyloxymethyl, 2-methylcarbonyloxyethyl, 2-ethylcarbonyloxyethyl, 3-methylcarbonyloxypropyl, 3-ethylcarbonyloxypropyl, 4-methylcarbonyloxybutyl, 4 -ethylcarbonyloxybutyl, sulfomethyl, 2-sulfoethyl, 3-sulfopropyl, 4-sulfobutyl, sulfamoylmethyl, 2-sulfamoylethyl, 3-sulfamoylpropyl and 4 -sulfamoylbutyl. Among them, particularly preferred $R^1$ and $R^2$ are hydrogen and lower alkyl and, particularly inter alia, preferred $R^1$ is hydrogen, methyl or ethyl and preferred $R^2$ is hydrogen.

When Y is —$CH_2CH_2Z$, Z is preferably sulfate ester or halogen. Particularly preferred Y is —CH=$CH_2$ or —$CH_2CH_3OSO_3H$.

A sulfate, thiosulfate, phosphate, carboxylate or acetate ester typically has up to 6, preferably up to 4, carbon atoms. An acyl group or moiety typically has up to 6, preferably up to 4, carbon atoms.

Among the compounds represented by the formula (I), preferred compounds include those the free acid form of which are represented by the following general formula (V):

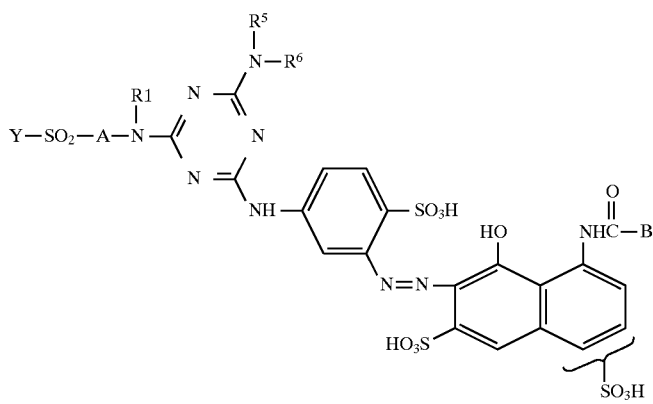

(V)

wherein A, B, $R^1$, $R^5$, $R^6$ and Y are as defined above

Particularly preferred compounds are those wherein A is ethylene, trimethylene or —$CH_2CH_2$—O—$CH_2CH_2$—, B is $C_1$–$C_4$ alkyl which may be substituted with carboxy or halogen, or β-carboxyvinyl, or is phenyl which may be substituted with one or two substituents selected from the group consisting of $C_1$–$C_4$ alkyl, $C_1$–$C_4$ alkoxy, carboxy, sulfo, nitro or halogeno, $R^1$ is hydrogen, methyl or ethyl, $R^5$ is hydrogen, methyl or ethyl and $R^6$ is phenyl which may be substituted with $C_1$–$C_4$ alkyl, $C_1$–$C_4$ alkoxy, sulfo, carboxy, halogeno, hydroxy, cyano or acylamino.

The compounds of the present invention may exist either in the free acid form or in the salt form. Particularly preferred are alkali metal salts and alkaline earth metal salts, such as, sodium salt, potassium salt and lithium salt thereof.

The compounds of the present invention can be produced by the following process. Briefly, a monoazo intermediate the free acid form of which is represented by the following general formula (VI):

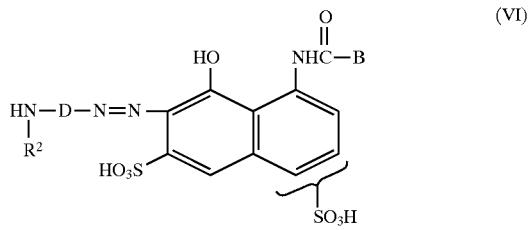

(VI)

wherein B, D and $R^2$ are as defined above, an aliphatic amine compound represented by the following general formula (VII):

(VII)

wherein A, $R^1$ and Y are as defined above, a compound represented by the following general formula (VIII):

(VIII)

wherein X is as defined above, and 2,4,6-trihalogeno-s-triazine are condensed to give the compound of the general formula (I).

In the condensation reaction with 2,4,6-trihalogeno-s-triazine, the order of condensation is not particularly limited but generally preferred order is one in which the compounds of the formulae (VII) and (VIII) are condensed with the compound at the first or second reaction and thereafter the monoazo intermediate of the formula (VI) is condensed in a third reaction. The conditions for condensation reaction are not particularly limited and the compound of the formula (I) or a salt thereof can be obtained by carrying out the first reaction at −10° C. to 40° C. at ph of 1 to 10, the second reaction at 0° C. to 70° C. at pH of 2 to 10 and the third reaction, at 10° C. to 100° C. at pH of 2 to 9.

The compounds of the present invention can also be produced by the following process. Briefly, in place of the monoazo intermediate of the general formula (VI) used in the above process, a diamine compound of the following general formula (IX):

(IX)

wherein D and $R^2$ are as defined above, can be used as a condensing component to produce, according to the same manner to that in the above process, an amine compound of the following general formula (X):

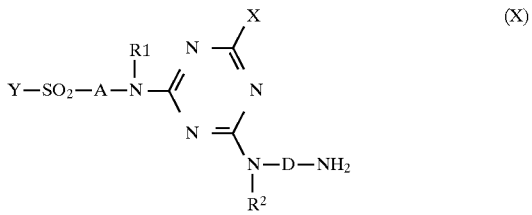

(X)

wherein A, D, $R^1$, $R^2$, X and Y are as defined above, which is diazotized according to the conventional method thereafter, and the resulting compound is coupled with a compound the free acid form of which is represented by the following general formula (XI):

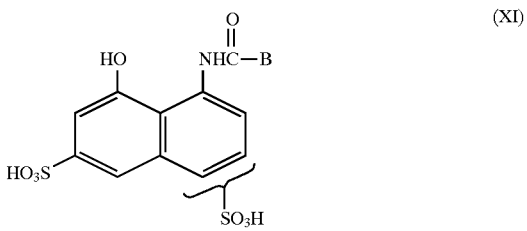

(XI)

wherein B is as defined above, in weakly acidic to weakly alkaline conditions to give the compound of the general formula (I).

Further, in another method, an amine compound represented by any one of the following general formulae (XII), (XIII) and (XIV):

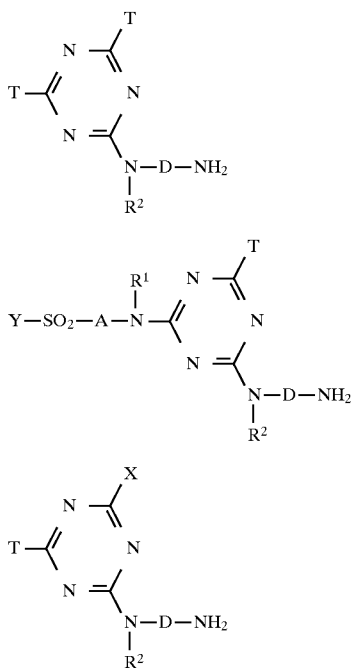

wherein A, D, $R^1$, $R^2$, X and Y are as defined above and T is halogen, can be diazotized according to the conventional method, followed by being coupled with a compound represented by the general formula (XI) in weakly acidic to weakly alkaline conditions and then condensed with the amine compound of the general formula (VII) and/or amine compound of the general formula (VIII) to give the compound of the general formula (I).

When the group represented by Y in the general formula (I) is —$CH_2CH_2Z$ wherein Z is as defined above, the ester group may be formed after the condensation reaction or the coupling reaction. In other words, in place of the compound of the general formula (VII) used in the production of the compound of the present invention, an amine compound of the following general formula (VIIa):

wherein A and $R^1$ is as defined above, can be used in the synthesis described above to give a precursor of the ester compound, which is then esterified to give the compound of the general formula (I).

As the starting material 2,4,6-trihalogeno-s-triazine, cyanuric chloride and cyanuric fluoride are particularly preferred.

Since the compounds of the present invention have a reactivity to fibers, they can be used for dyeing or printing organic materials containing hydroxyl group and/or amido group. Said organic materials are preferably used in the form of fiber materials or mixed yarn thereof.

The organic materials containing hydroxyl group include natural or synthetic one such as cellulose fiber materials or regenerated fibers thereof and polyvinyl alcohol. Preferred cellulose fiber materials include cotton or other plant fibers such as linen, hemp, jute and ramie fibers. Regenerated fibers materials include, for example, viscose staple and filament viscose.

The organic materials containing amido group include, for example, natural polyamide, polyurethane, leather and the like. Specific examples include fiber materials such as wool, other animal fibers, silk, polyamide-6,6, polyamide-6, polyamide-11 and polyamide-4.

The compounds of the present invention can be used for dyeing or printing the above materials, particularly fiber materials, by a method according to physicochemical properties of individual materials.

For example, when a cellulose fiber material is dyed by exhaustion, the dyeing is carried out at a relatively low temperature in the presence of an acid binding agent such as sodium carbonate, trisodium phosphate and sodium hydroxide and sometimes with addition of a neutral salt such as sodium sulfate or sodium chloride as well as, if desired, dissolution aid, penetrating agent or levelling agent. The neutral salt for promoting exhaustion of dye can be added after or before the desired temperature is attained or sometimes in portions.

When a cellulose fiber material is dyed by padding, the padding can be carried out at the room temperature or an elevated temperature and the dye can be fixed by steaming or dry-heating after drying.

When a cellulose fiber material is printed, the printing can be carried out by the one phase process in which the material is printed with a printing paste containing an acid binding agent, such as sodium hydrogen carbonate or the like followed by being subjected to steaming at 95°–160° C., or by the two-phase process in which the material is printed with, for example, a neutral or weakly acidic printing paste followed by being passed through a hot electrolyte-containing alkaline bath or over-padded with an alkaline electrolyte-containing padding solution followed by being subjected to steaming or dry-heating.

The printing paste may contain a paste such as sodium alginate or starch ether or a emulsifier together with, if desired, a conventional printing aid such as urea and/or a dispersing agent.

The acid binding agent suitable for fixing the compounds of the invention on cellulose fibers may be, for example, an alkali metal hydroxide, a water soluble basic salt of an alkali metal or alkaline earth metal with an inorganic or organic acid, or a compound which separates an alkali under heat. Particularly, the agent includes alkali metal hydroxides and alkali metal salts of a weak- or medium-acidic inorganic or organic acid. Among them, sodium or potassium hydroxide and sodium or potassium salts are preferred. Specific examples of the acid binding agent include sodium hydroxide, potassium hydroxide, sodium hydrogen carbonate, sodium carbonate, sodium formate, potassium carbonate, mono-, di- or tri-sodium phosphate, sodium silicate and sodium trichloroacetate.

Dyeing of synthetic or natural polyamide or urethane fibers can be carried out by exhausting the dye in an acidic or weakly acidic dye bath under controlling of pH and then changing pH to a neutral or sometimes to alkaline region in order to fixing the dye. The dyeing can be carried out usually at 60° C. to 120° C. In order to attain a level dyeing, conventional levelling agents such as a condensation product of cyanuric chlorine and thrice molar aminobenzene sulfonic acid or aminonaphthalene sulfonic acid and an addition product of stearyl amine and ethylene oxide can be used.

The compounds of the present invention have characteristics that they exhibit excellent properties in dyeing and printing of fiber materials. They are particularly suitable for dyeing cellulose fiber materials and dyed products obtained by using the compounds have good light fastness and perspiration light fastness, excellent wetting fastness such as washing fastness and peroxide washing fastness, chlorine fastness, perspiration fastness and acid-hydrolysis fastness and alkali fastness, as well as good abrasion fastness and ironing fastness.

Further, they have characteristics that they have excellent dyeing ability, build-up properties, levelness and wash-off properties, and good solubility and exhaustion/fixing properties, and that they are hardly affected by changes in dyeing temperature, amount of auxiliaries such as salts or alkaline agents and liquor ratio, and give dyed products with stable quality.

They also have characteristics that they are less causative of color change of the dyed product during fixation treatment or resin finishing and of change upon contact with a basic substance during storage.

Furthermore, they exhibit excellent build-up properties and excellent alkali stability in cold batch-up dyeing, show almost no difference in depth and color between fixing at low temperature and fixing at 25° C. and are characterized in that they are less sensitive to hydrolysis by an alkaline agent.

While the compounds of the present invention give red to scarlet color by itself to fiber materials, they can be used, if necessary, for obtaining other desired color by mixing with other dyes. Said other dyes for mixing are not particularly limited and may be any reactive dyes. Examples of the reactive dyes include those commercialized under trade names Sumifix, Sumifix Supra, Remazol, Levafix, Procion, Cibacron and the like and dyes described in JP-A-56-9483, JP-A-56-12820, JP-A-56-143360, JP-A-57-2365, JP-A-58-191755, JP-A-59-96174, JP-A-60-123559, JP-A-61-155469, JP-A-63-77974, JP-A-63-225665, JP-A-1-185370 or JP-A-3-770.

The compounds of the present invention have high fixing ability, i. e. excellent build-up properties, in deep color dyeing as red dyes for organic materials having hydroxy group and/or amido group.

EXAMPLES

The present invention will now be illustrated in further detail by means of Examples, which should not be construed as limitation upon the scope of the invention. In the Examples, parts means parts by weight.

EXAMPLE 1

According to the conventional method, 18.8 parts of 2,4-diaminobenzenesulfonic acid and 18.4 parts of cyanuric chloride were condensed at a pH of 2–4 and a temperature of 0°–15° C. Then, 23.3 parts of 2-(β-hydroxyethylsulfonyl) ethylamine was condensed therewith at a pH of 4–8 and a temperature of 10°–40° C. The product was diazotized according to the conventional method and then the product was coupled with 36.1 parts of 1-acetylamino-8-hydroxynaphthalene-3, 6-disulfonic acid at a pH of 3–8 and a temperature of 0°–15° C. Further, 9.3 parts of aniline was condensed therewith at a pH of 2–6 and a temperature of 30°–70° C. The obtained product was converted to sulfonate ester according to the conventional method and the product was salted out to give a monoazo compound the free acid form of which is represented by the following formula:

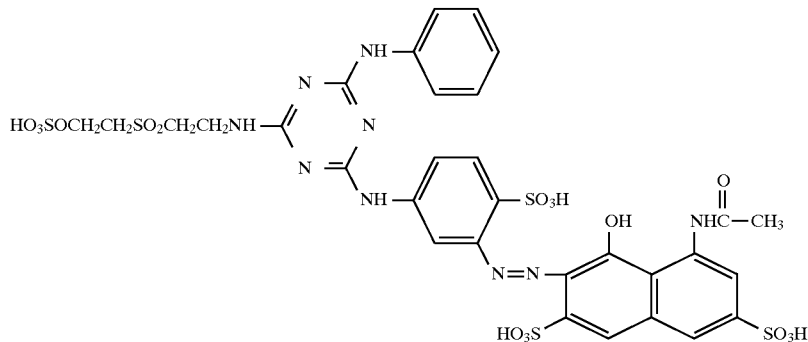

($\lambda_{MAX}$=510 nm, in an aqueous medium)

EXAMPLE 2

Using compounds shown in column 2, column 3, column 4 and column 5 of the following Table in place of 2-(β-hydroxyethylsulfonyl)ethylamine, aniline, 2,4-diaminobenzene-sulfonic acid and 1-acetylamino-8-hydroxynaphthalene-3, 6-disulfonic acid used in Example 1, respectively, corresponding monoazo compounds were synthesized in a manner similar to that in Example 1 and used for dyeing. Dyed products having respective colors shown in column 6 of the Table were obtained.

The same results were obtained when the order of the first condensation and second condensation to cyanuric chloride in the above syntheses was exchanged. Also, the same results were obtained when corresponding sulfate esters were used in place of compounds in column 2 and the sulfating of last step was omitted.

TABLE 1

| | column 2 | column 3 | column 4 | column 5 | column 6 |
|---|---|---|---|---|---|
| 1 | $HOC_2H_4SO_2C_3H_6NH_2$ | aniline | 2,4-diaminobenzenesulfonic acid | 5-hydroxy-8-acetamido-naphthalene-2,7-disulfonic acid | Red |
| 2 | $HOC_2H_4SO_2C_3H_6NH_2$ | 3-aminobenzenesulfonic acid | 2,4-diaminobenzenesulfonic acid | 5-hydroxy-8-propionamido-naphthalene-2,7-disulfonic acid | Red |
| 3 | $HOC_2H_4SO_2C_2H_4NH_2$ | 3-aminobenzenesulfonic acid | 2,4-diaminobenzenesulfonic acid | 5-hydroxy-8-propionamido-naphthalene-2,7-disulfonic acid | Red |
| 4 | $HOC_2H_4SO_2C_2H_4NH_2$ | N-ethyl-4-chloroaniline | 2,5-diaminobenzenesulfonic acid | 5-hydroxy-8-(3-carboxypropionamido)-naphthalene-2,7-disulfonic acid | Red |
| 5 | $HOC_2H_4SO_2C_2H_4NH_2$ | 4-aminobenzoic acid | 2,5-diaminobenzenesulfonic acid | 5-hydroxy-8-propionamido-naphthalene-2,7-disulfonic acid | Red |

TABLE 2

| | column 2 | column 3 | column 4 | column 5 | column 6 |
|---|---|---|---|---|---|
| 6 | $HOC_2H_4SO_2C_3H_6NH_2$ | 3-aminobenzenesulfonic acid | 4-methyl-2-amino-5-sulfoaniline | 5-hydroxy-8-acetamido-naphthalene-2,6-disulfonic acid | Red |
| 7 | $HOC_2H_4SO_2C_2H_4NH_2$ | 4-ethylaniline | 2,4-diaminobenzenesulfonic acid | 5-hydroxy-8-propionamido-naphthalene-2,7-disulfonic acid | Red |
| 8 | $HOC_2H_4SO_2C_2H_4NH_2$ | 2-aminobenzoic acid | 2,4-diaminobenzenesulfonic acid | 5-hydroxy-8-propionamido-naphthalene-2,7-disulfonic acid | Red |
| 9 | $HOC_2H_4SO_2CH_2CH_2O-$<br>$-CH_2CH_2NH_2$ | N-methyl-3-hydroxyaniline | 2,4-diaminobenzenesulfonic acid | 5-hydroxy-8-(chloroacetamido)-naphthalene-2,7-disulfonic acid | Red |

TABLE 2-continued

| | column 2 | column 3 | column 4 | column 5 | column 6 |
|---|---|---|---|---|---|
| 10 | HOC$_2$H$_4$SO$_2$CH$_2$CH$_2$O—CH$_2$CH$_2$NH$_2$ | 2-methylaniline (o-toluidine, H$_2$N, CH$_3$) | 4-methyl-2-amino-benzenesulfonic acid (H$_2$NCH$_2$, CH$_3$, SO$_3$H, NH$_2$) | 8-hydroxy-1-(3-carboxypropanoylamino)-naphthalene-3,5-disulfonic acid (HO, NHCOCH$_2$CH$_2$CO$_2$H, HO$_3$S, SO$_3$H) | Red |

TABLE 3

| | column 2 | column 3 | column 4 | column 5 | column 6 |
|---|---|---|---|---|---|
| 11 | HOC$_2$H$_4$SO$_2$CH$_2$CH$_2$NH$_2$ | aniline (H$_2$N-phenyl) | 2,4-diaminobenzenesulfonic acid (H$_2$N, SO$_3$H, NH$_2$) | 8-hydroxy-1-(chloroacetylamino)-naphthalene-3,6-disulfonic acid (HO, NHCOCH$_2$Cl, HO$_3$S, SO$_3$H) | Red |
| 12 | HOC$_2$H$_4$SO$_2$CH$_2$CH$_2$NH$_2$ | aniline (H$_2$N-phenyl) | 2,4-diaminobenzenesulfonic acid (H$_2$N, SO$_3$H, NH$_2$) | 8-hydroxy-1-(propanoylamino)-naphthalene-3,6-disulfonic acid (HO, NHCOC$_2$H$_5$, HO$_3$S, SO$_3$H) | Red |
| 13 | HOC$_2$H$_4$SO$_2$CH$_2$CH$_2$NH$_2$ | 4-aminophenol (H$_2$N-phenyl-OH) | 2,4-diaminobenzenesulfonic acid (H$_2$N, SO$_3$H, NH$_2$) | 8-hydroxy-1-(propanoylamino)-naphthalene-3,6-disulfonic acid (HO, NHCOC$_2$H$_5$, HO$_3$S, SO$_3$H) | Red |
| 14 | HOC$_2$H$_4$SO$_2$CH$_2$CH$_2$NH$_2$ | N-ethylaniline (C$_2$H$_5$-HN-phenyl) | 2,4-diaminobenzenesulfonic acid (H$_2$N, SO$_3$H, NH$_2$) | 8-hydroxy-1-(propanoylamino)-naphthalene-3,6-disulfonic acid (HO, NHCOC$_2$H$_5$, HO$_3$S, SO$_3$H) | Red |
| 15 | HOC$_2$H$_4$SO$_2$CH$_2$CH$_2$NH$_2$ | 2-ethylaniline (C$_2$H$_5$, H$_2$N-phenyl) | 2,4-diaminobenzenesulfonic acid (H$_2$N, SO$_3$H, NH$_2$) | 8-hydroxy-1-(propanoylamino)-naphthalene-3,6-disulfonic acid (HO, NHCOC$_2$H$_5$, HO$_3$S, SO$_3$H) | Red |

TABLE 4

| | column 2 | column 3 | column 4 | column 5 | column 6 |
|---|---|---|---|---|---|
| 16 | HOC$_2$H$_4$SO$_2$C$_3$H$_6$NH$_2$ | 3-aminobenzenesulfonic acid (H$_2$N-phenyl-SO$_3$H) | 2,4-diaminobenzenesulfonic acid (H$_2$N, SO$_3$H, NH$_2$) | 8-hydroxy-1-(3-carboxy-2-propenoylamino)-naphthalene-3,5-disulfonic acid (HO, NHCOCH=CHCO$_2$H, HO$_3$S, SO$_3$H) | Red |
| 17 | HOC$_2$H$_4$SO$_2$C$_3$H$_6$NH$_2$ | 3-aminobenzenesulfonic acid (H$_2$N-phenyl-SO$_3$H) | 2,4-diaminobenzenesulfonic acid (H$_2$N, SO$_3$H, NH$_2$) | 8-hydroxy-1-(carboxymethyleneaminocarbonyl)-naphthalene-3,6-disulfonic acid (HO, NHCOCH=CHOO$_2$H, HO$_3$S, SO$_3$H) | Red |

TABLE 4-continued

| | column 2 | column 3 | column 4 | column 5 | column 6 |
|---|---|---|---|---|---|
| 18 | HOC$_2$H$_4$SO$_2$C$_2$H$_4$NH$_2$ | 3-aminobenzoic acid (H$_2$N, CO$_2$H on benzene) | 4-methoxy-2-amino-5-aminobenzenesulfonic acid (OCH$_3$, H$_2$N, SO$_3$H, NH$_2$) | 8-hydroxy-5-(3-chloropropanoylamino)naphthalene-3,6-disulfonic acid (HO, NHCOCH$_2$CH$_2$Cl, HO$_3$S, SO$_3$H) | Red |
| 19 | HOC$_2$H$_4$SO$_2$C$_2$H$_4$NH$_2$ | N-methylaniline (CH$_3$NH-phenyl) | 2,5-diaminobenzenesulfonic acid (SO$_3$H, H$_2$N, NH$_2$) | 8-hydroxy-5-acetylaminonaphthalene-3,? -disulfonic acid (HO, NHCOCH$_3$, HO$_3$S, SO$_3$H) | Red |
| 20 | HOC$_2$H$_4$SO$_2$C$_2$H$_4$O—<br>—C$_2$H$_4$NH$_2$ | 2,5-diaminobenzene-1,4-disulfonic acid (SO$_3$H, H$_2$N, SO$_3$H) | 2,5-diaminobenzenesulfonic acid (SO$_3$H, H$_2$N, NH$_2$) | 8-hydroxy-5-acetylaminonaphthalene-3,?-disulfonic acid (HO, NHCOCH$_3$, HO$_3$S, SO$_3$H) | Red |

TABLE 5

| | column 2 | column 3 | column 4 | column 5 | column 6 |
|---|---|---|---|---|---|
| 21 | HOC$_2$H$_4$SO$_2$C$_2$H$_4$NH(CH$_3$) | 6-amino-2-naphthalenesulfonic acid (H$_2$N, SO$_3$H) | 2,5-diamino-benzenesulfonic acid (H$_2$N, SO$_3$H, NH$_2$) | 8-hydroxy-5-acetylaminonaphthalene-3,6-disulfonic acid (HO, NHCOCH$_3$, HO$_3$S, SO$_3$H) | Red |
| 22 | HOC$_2$H$_4$SO$_2$C$_2$H$_4$O—<br>—C$_2$H$_4$NH$_2$ | piperidine (HN ring) | 2,5-diamino-benzenesulfonic acid (H$_2$N, NH$_2$, SO$_3$H) | 8-hydroxy-5-(2-chloroacetylamino)naphthalene-3,6-disulfonic acid (HO, NHCOC$_2$H$_4$Cl, HO$_3$S, SO$_3$H) | Red |
| 23 | HOC$_2$H$_4$SO$_2$C$_3$H$_6$NH$_2$ | pyrrolidine (HN ring) | 4-methyl-2-amino-5-aminobenzenesulfonic acid (CH$_3$, H$_2$N, SO$_3$H, NH$_2$) | 8-hydroxy-5-(3-carboxypropanoylamino)naphthalene-3,6-disulfonic acid (HO, NHCOCH$_2$CH$_2$CO$_2$H, HO$_3$S, SO$_3$H) | Red |
| 24 | HOC$_2$H$_4$SO$_2$C$_3$H$_6$NH$_2$ | H$_2$NCH$_3$ | 4-methyl-2-amino-5-aminobenzenesulfonic acid (CH$_3$, H$_2$N, SO$_3$H, NH$_2$) | 8-hydroxy-5-(3-carboxypropanoylamino)naphthalene-3,6-disulfonic acid (HO, NHCOCH$_2$CH$_2$CO$_2$H, HO$_3$S, SO$_3$H) | Red |
| 25 | HOC$_2$H$_4$SO$_2$C$_2$H$_4$NH$_2$ | H$_2$NC$_2$H$_4$CONH$_2$ | 4-methyl-2-amino-5-aminobenzenesulfonic acid (CH$_3$, H$_2$N, SO$_3$H, NH$_2$) | 8-hydroxy-5-propionylaminonaphthalene-3,6-disulfonic acid (HO, NHCOC$_2$H$_5$, HO$_3$S, SO$_3$H) | Red |

TABLE 6

| | column 2 | column 3 | column 4 | column 5 | column 6 |
|---|---|---|---|---|---|
| 26 | $HOC_2H_4SO_2C_2H_4NH_2$ | aniline ($H_2N$-phenyl) | 2,4-diaminobenzenesulfonic acid ($H_2N$-C$_6$H$_3$(SO$_3$H)(NH$_2$)) | 8-hydroxy-1-benzamido-naphthalene-3,6-disulfonic acid | Red |
| 27 | $HOC_2H_4SO_2C_2H_4NH_2$ | 4-aminophenol ($H_2N$-C$_6$H$_4$-OH) | 2,4-diaminobenzenesulfonic acid | 8-hydroxy-1-benzamido-naphthalene-3,6-disulfonic acid | Red |
| 28 | $HOC_2H_4SO_2C_2H_4NH_2$ | anthranilic acid (2-$H_2N$-C$_6$H$_4$-CO$_2$H) | 2,4-diaminobenzenesulfonic acid | 8-hydroxy-1-benzamido-naphthalene-3,6-disulfonic acid | Red |
| 29 | $HOC_2H_4SO_2C_2H_4NH_2$ | 2-ethylaniline (2-$C_2H_5$-C$_6$H$_4$-NH$_2$) | 2,4-diaminobenzenesulfonic acid | 8-hydroxy-1-benzamido-naphthalene-3,6-disulfonic acid | Red |
| 30 | $HOC_2H_4SO_2C_2H_4NH_2$ | 2-aminobenzene-1,4-disulfonic acid | 2,4-diaminobenzenesulfonic acid | 8-hydroxy-1-benzamido-naphthalene-3,6-disulfonic acid | Red |

TABLE 7

| | column 2 | column 3 | column 4 | column 5 | column 6 |
|---|---|---|---|---|---|
| 31 | $HOC_2H_4SO_2C_2H_4NH_2$ | 3-aminobenzenesulfonic acid | 2,4-diaminobenzenesulfonic acid | 8-hydroxy-1-(4-chlorobenzamido)-naphthalene-3,6-disulfonic acid | Red |
| 32 | $HOC_2H_4SO_2C_2H_4NH_2$ | anthranilic acid (2-$H_2N$-C$_6$H$_4$-CO$_2$H) | 2,4-diaminobenzenesulfonic acid | 8-hydroxy-1-(4-chlorobenzamido)-naphthalene-3,6-disulfonic acid | Red |
| 33 | $HOC_2H_4SO_2C_2H_4NH_2$ | aniline ($H_2N$-phenyl) | 2,4-diaminobenzenesulfonic acid | 8-hydroxy-1-(4-chlorobenzamido)-naphthalene-3,6-disulfonic acid | Red |

TABLE 7-continued

| | column 2 | column 3 | column 4 | column 5 | column 6 |
|---|---|---|---|---|---|
| 34 | HOC$_2$H$_4$SO$_2$C$_2$H$_4$NH$_2$ | H$_2$N–C$_6$H$_5$ | 2,4-diamino benzenesulfonic acid (H$_2$N–, –SO$_3$H, –NH$_2$) | 8-hydroxy-1-(2-sulfophenylamido)naphthalene-3,6-disulfonic acid derivative | Red |
| 35 | HOC$_2$H$_4$SO$_2$C$_2$H$_4$N(CH$_3$)H | H$_2$N–C$_6$H$_5$ | 2,4-diamino benzenesulfonic acid | 8-hydroxy-1-(2-sulfophenylamido)naphthalene-3,6-disulfonic acid derivative | Red |

TABLE 8

| | column 2 | column 3 | column 4 | column 5 | column 6 |
|---|---|---|---|---|---|
| 36 | HOC$_2$H$_4$SO$_2$C$_3$H$_6$N(C$_2$H$_5$)H | 4-Cl–C$_6$H$_4$–NH(C$_2$H$_5$) | 2,4-diamino benzenesulfonic acid | 8-hydroxy-1-(4-carboxyphenylamido)naphthalene-3,5-disulfonic acid derivative | Red |
| 37 | HOC$_2$H$_4$SO$_2$C$_3$H$_6$NH$_2$ | 3-CH$_3$–C$_6$H$_4$–NH$_2$ | 2,4-diamino benzenesulfonic acid | 8-hydroxy-1-(phenylamido)naphthalene-3,5-disulfonic acid derivative | Red |
| 38 | HOC$_2$H$_4$SO$_2$C$_3$H$_6$NH$_2$ | 2,5-disulfo aniline | 2,4-diamino benzenesulfonic acid | 8-hydroxy-1-(phenylamido)naphthalene-3,5-disulfonic acid derivative | Red |
| 39 | HOC$_2$H$_4$SO$_2$C$_2$H$_4$O–C$_2$H$_4$NH$_2$ | 2,5-disulfo aniline | 2,4-diamino benzenesulfonic acid | 8-hydroxy-1-(4-methylphenylamido)naphthalene-3,6-disulfonic acid derivative | Red |
| 40 | HOC$_2$H$_4$SO$_2$C$_2$H$_4$O–C$_2$H$_4$NH$_2$ | H$_2$N–C$_6$H$_5$ | 2,4-diamino benzenesulfonic acid | 8-hydroxy-1-(4-methylphenylamido)naphthalene-3,6-disulfonic acid derivative | Red |

TABLE 9

| | column 2 | column 3 | column 4 | column 5 | column 6 |
|---|---|---|---|---|---|
| 41 | HOC₂H₄SO₂C₃H₈NH₂ | N-methylaniline | 4-methoxy-1,3-diaminobenzene-6-sulfonic acid | 8-hydroxy-5-(3,5-dichlorobenzamido)naphthalene-3,6-disulfonic acid | Red |
| 42 | HOC₂H₄SO₂C₃H₈NH₂ | 4-aminobenzoic acid | 4-methyl-1,3-diaminobenzene-6-sulfonic acid | 8-hydroxy-5-(3,5-dichlorobenzamido)naphthalene-3,6-disulfonic acid | Red |
| 43 | HOC₂H₄SO₂C₂H₄NH₂ | 3-aminobenzenesulfonic acid | 4-methyl-1,3-diaminobenzene-6-sulfonic acid | 8-hydroxy-5-(4-nitrobenzamido)naphthalene-3,6-disulfonic acid | Red |
| 44 | HOC₂H₄SO₂C₂H₄NH₂ | aniline | 2,4-diaminobenzenesulfonic acid | 8-hydroxy-5-(2-sulfobenzamido)naphthalene-3,6-disulfonic acid | Red |
| 45 | HOC₂H₄SO₂C₂H₄NH₂ | 4-aminophenol | 2,4-diaminobenzenesulfonic acid | 8-hydroxy-5-(4-ethylbenzamido)naphthalene-3,6-disulfonic acid | Red |

TABLE 10

| | column 2 | column 3 | column 4 | column 5 | column 6 |
|---|---|---|---|---|---|
| 46 | HOC₂H₄SO₂C₂H₄O—C₂H₄NH₂ | 7-aminonaphthalene-1,5-disulfonic acid | 2,4-diaminobenzenesulfonic acid | 8-hydroxy-5-benzamidonaphthalene-3,6-disulfonic acid | Red |

TABLE 10-continued

| | column 2 | column 3 | column 4 | column 5 | column 6 |
|---|---|---|---|---|---|
| 47 | HOC$_2$H$_4$SO$_2$C$_3$H$_6$NH$_2$ | piperidine (HN) | H$_2$N—C$_6$H$_3$(SO$_3$H)—NH$_2$ | HO, NHCO-phenyl naphthalene with HO$_3$S and SO$_3$H | Red |
| 48 | HOC$_2$H$_4$SO$_2$C$_2$H$_4$N(CH$_3$)H | morpholine (HN—O) | H$_2$N—C$_6$H$_3$(SO$_3$H)—NH$_2$ | HO, NHCO-(4-CH$_3$-phenyl) naphthalene with HO$_3$S and SO$_3$H | Red |
| 49 | HOC$_2$H$_4$SO$_2$C$_2$H$_4$N(CH$_3$)H | H$_2$NC$_2$H$_5$ | CH$_3$-C$_6$H$_2$(H$_2$N)(SO$_3$H)(NH$_2$) | HO, NHCO-phenyl naphthalene with HO$_3$S and SO$_3$H | Red |
| 50 | HOC$_2$H$_4$SO$_2$C$_3$H$_8$NH$_2$ | H$_2$NCH$_2$CH$_2$OH | CH$_3$-C$_6$H$_2$(H$_2$N)(SO$_3$H)(NH$_2$) | HO, NHCO-phenyl naphthalene with HO$_3$S and SO$_3$H | Red |

Dyeing Example 1

Each 0.3 part of monoazo compounds obtained in Examples 1 or 2 was dissolved in 200 parts of water. Then 20 parts of sodium sulfate and 10 parts of cotton were added to the resulting solutions and the solutions were heated to 60° C. After 30 minutes, 4 parts of sodium carbonate was added and dyeing was effected for an hour at this temperature. Upon completion of dyeing, the products were subjected to rinsing and soaping to give respective vivid red dyed products excellent in various fastness and having a good build-up properties.

Dyeing Example 2

Using compounds obtained in Examples 1 or 2, color pastes having the following compositions were prepared.

| | |
|---|---|
| Monoazo compound | 5 parts |
| Urea | 5 parts |
| Sodium alginate | 50 parts |
| Hot water | 25 parts |
| Sodium hydrogen carbonate | 2 parts |
| Water (balance) | 13 parts |

Each of the color pastes were printed onto a mercerized cotton broad cloth, which was subjected to intermediate drying, steaming at 100° C. for 5 minutes, rinsing with warm water, soaping, rinsing with warm water and drying, in this order, to give a vivid red printed product excellent in various fastness.

What is claimed is:

1. A monoazo compound represented by the general formula (I):

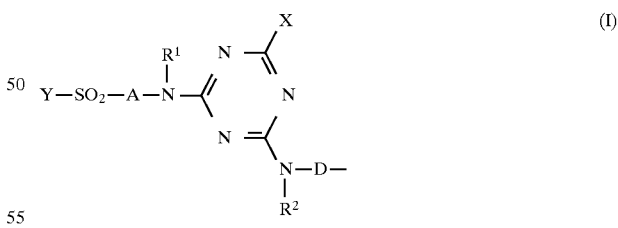

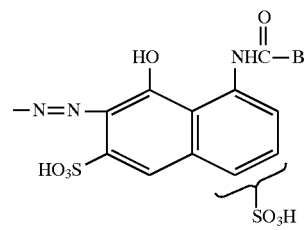

wherein A represents alkylene which may be substituted or a group: —(CH$_2$)m—Q$^1$—(CH$_2$)n— wherein $Q^1$ is —O—, —S— or —NR$^3$—, m and n are, independently of each other, 2, 3 or 4 and $R^3$ is hydrogen, alkyl which may be substituted or phenyl which may be substituted;

B represents β-carboxyvinyl, alkyl which may be substituted or phenyl which may be substituted;

D represents a group of the formula (II):

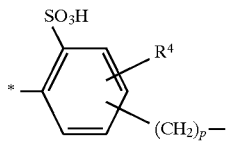 (II)

wherein * represents a bond connecting to the azo group in the formula (I), $R^4$ is hydrogen, methyl or methoxy and p is 0 or 1;

X represents a group of the formula (III) or (IV):

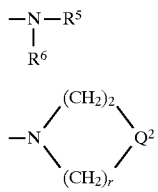 (III) (IV)

wherein $R^5$ and $R^6$ are, independently of each other, hydrogen, alkyl which may be substituted, phenyl which may be substituted or naphthyl which may be substituted, r is 1, 2 or 3, $Q^2$ is —O—, —S—, —CH$_2$—, —SO$_2$— or —NR$^7$— in which $R^7$ is hydrogen or alkyl which may be substituted;

$R^1$ and $R^2$ are, independently of each other, hydrogen or alkyl which may be substituted; and Y is a group: —CH=CH$_2$ or —CH$_2$CH$_2$Z wherein Z is the radical of a sulfate ester, a thiosulfate ester, a phosphate ester or an acetate ester, or a halogen atom; or a salt thereof.

2. A monoazo compound according to claim 1, in which X is the group of formula (III), or a salt thereof.

3. A monoazo compound according to claim 2, in which one of $R^5$ and $R^6$ is methyl or ethyl and the other is phenyl which may be substituted, or a salt thereof.

4. A monoazo compound according to claim 1, in which A is ethylene, trimethylene or —CH$_2$CH$_2$—O—CH$_2$CH$_2$—, or a salt thereof.

5. A monoazo compound according to claim 1, in which B is $C_1$–$C_4$ alkyl which may be substituted with carboxy or halogen, or is β-carboxyvinyl, or a salt thereof.

6. A monoazo compound according to claim 1, in which B is phenyl which may be substituted with 1 or 2 substituents selected from the group consisting of $C_1$–$C_4$ alkyl, $C_1$–$C_4$ alkoxy, carboxy sulfo, nitro or halogeno, or a salt thereof.

7. A monoazo compound according to claim 1, in which p is 0, or a salt thereof.

8. A monoazo compound according to claim 1, in which $R^1$ and $R^2$ are, independently of each other, hydrogen, methyl or ethyl, or a salt thereof.

9. A monoazo compound according to claim 1, in which Y is —CH=CH$_2$ or —CH$_2$CH$_2$OSO$_3$H, or a salt thereof.

10. A process for dyeing or printing a fiber material which comprises contacting the material with a monoazo compound according to claim 1 or a salt thereof.

* * * * *